US005173405A

United States Patent [19]

Simons, Jr.

[11] Patent Number: 5,173,405

[45] Date of Patent: Dec. 22, 1992

[54] USE OF ARSENITE TO REVERSIBLY BLOCK STEROID BINDING TO GLUCOCORTICOID RECEPTORS IN THE PRESENCE OF OTHER STEROID RECEPTORS

[75] Inventor: S. Stoney Simons, Jr., Bethesda, Md.

[73] Assignee: The United States of America as represented by the Department of Health and Human Services, Washington, D.C.

[21] Appl. No.: 584,758

[22] Filed: Sep. 19, 1990

Related U.S. Application Data

[63] Continuation-in-part of Ser. No. 468,929, Jan. 23, 1990, abandoned.

[51] Int. Cl.$^5$ .......... G01N 33/574

[52] U.S. Cl. .......... 435/7.23; 435/7.21; 435/7.7; 435/962; 435/975; 436/503; 436/504; 436/817; 436/825

[58] Field of Search .......... 435/7.23, 7.7, 962, 435/7.92, 975, 7.21; 436/503, 504, 817, 825

[56] References Cited

PUBLICATIONS

Allegra et al., "Distribution Frequency, and Quantitative Analysis of Estrogen, Progesterone, Androgen and Glucocorticoid Receptors in Human Breast Cancer," Cancer Research, vol. 39, pp. 1457-1454, (1979).

Joshi et al., "Inhibition of Coupling Factor B Activity by Cadmium Ion, Arsenite-2,3-Dimercaptopropanol, and Phenylarsenine Oxide, and Preferential Reactivation by Dithiols", J. Biol. Chem. vol. 256, No. 21, pp. 11112-11116, (1981).

Moguilewsky et al., "Evidence for a Specific Mineralocorticoid Receptor in Rat Pituitary and Brain," J. Steroid Biochem, vol. 12, pp. 309-314, (1980).

Evans, Science, vol. 240, 889-895, 1988.

Northrop et al., Journal of Biological Chemistry, vol. 261, 11064-11070, 1986.

Martin et al., Proc. Natl. Acad. Sci., vol. 85, pp. 2533-2537, 1988.

Clark et al., N. Engl. J. Med., vol. 309, 1343-1347, 1983.

G. Teutsch et al., J. Steroid Biochem, vol. 31, No. 4B, pp. 549-565, 1988.

Simons, Jr. et al., The Journal of Biological Chemistry, vol. 258, No. 4, pp. 2229-2238, 1983.

Simons, Jr. et al., The Journal of Biological Chemistry, vol. 262, No. 20, pp. 9676-9680, 1987.

Miller et al., The Journal of Biological Chemistry, vol. 263, No. 29, pp. 15217-15229, 1988.

Simons, Jr. et al., The Journal of Biological Chemistry, vol. 265, No. 4, pp. 1938-1945, 1990.

Journal of Biol. Chem. vol. 262, No. 20, Jul. (1987) pp. 9669-9675, (Simons, Jr. et al).

Journal of Biol. Chem. vol. 265, No. 27, Sep. (1990) pp. 16039-16042, (Lopez et al).

Journal of Bio. Chem. vol. 265, No. 4, Feb. (1990). pp. 1938-1945. (Simons, Jr. et al.).

Biol. of the Cell, vol. 56, (1986) (Scarmato et al). pp. 255-258.

International Search Report.

*Primary Examiner*—Esther L. Kepplinger
*Assistant Examiner*—Susan C. Wolski
*Attorney, Agent, or Firm*—Birch, Stewart, Kolasch & Birch

[57] ABSTRACT

The present invention is directed to a method for selectively blocking or inactivating glucocorticoid receptors by administering a glucocorticoid receptor blocking effective amount of arsenite or methyl methanethiolsulfonate (MMTS) in a sample. Thus, arsenite and MMTS constitute new, simple, reversible, and inexpensive reagents for assaying glucocorticoid receptors in the presence of other receptors and for eliminating the complications of assaying other receptors in the presence of glucocorticoid receptors.

25 Claims, 7 Drawing Sheets

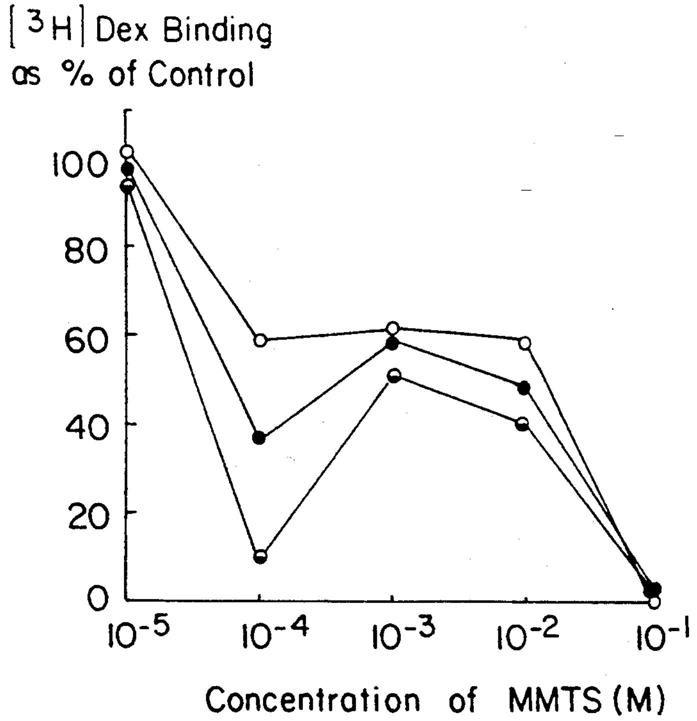
FIG. 1B
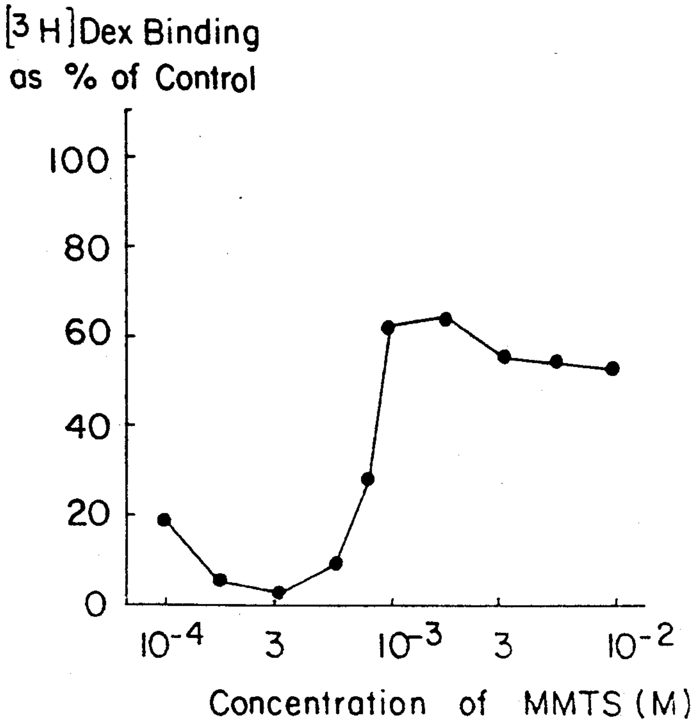

USE OF ARSENITE TO REVERSIBLY BLOCK STEROID BINDING TO GLUCOCORTICOID RECEPTORS IN THE PRESENCE OF OTHER STEROID RECEPTORS

This is a continuation-in-part of U.S. Ser. No 07/468,929 filed on Jan. 23, 1990, now abandoned, the entire contents of which are incorporated by reference.

BACKGROUND OF THE INVENTION

1. Field of the Invention

The present invention is directed to a method for selectively blocking glucocorticoid receptors by contacting the receptors with a glucocorticoid receptor blocking effective amount of arsenite or methyl methanethiolsulfonate (MMTS) to a sample.

2. Description of Related Art

A large number of responses to steroid hormones are mediated by the cognate receptor protein. In the absence of a functional, wild-type receptor, these responses to steroid hormones cannot be observed. For example, lymphocytes and leukemic cells are normally killed by glucocorticoids and many breast cancer cells are killed by estrogens; but, cell toxicity is not observed in leukemic cells lacking glucocorticoid receptors or in breast cancer cells lacking estrogen receptors. Similarly, patients resistant to vitamin D were found to have a point mutation in that region of the receptor protein that interacts with the DNA of regulated genes. Furthermore, the amount of functional receptor protein has been found to be important both for the level of hormone response and, when the target cell contains more than one type of receptor, for the type of receptor-mediated response which is observed. Thus quantitation of the amount of functional receptor in a given cell or tissue is crucial for predicting whether a steroid-induced response is possible and what the magnitude of that response will be.

The four current methods for detecting the presence of receptors vary in their ability to detect functional receptors. Receptor mRNA levels can be determined by quantitative Northern blots since the cDNAs of all of the steroid receptors have now been cloned (see Evans, Science, 240, 889–895, 1988 and references therein). However, this method cannot distinguish a priori between the mRNAs of functional and non-functional receptor proteins (Northrop et al., J. Biol. Chem., 261, 1106–11070, 1986) and cannot guarantee the presence of receptor protein. Quantitative Western blots with anti-receptor antibodies cannot distinguish between functional and non-functional proteins (Martin et al., Proc. Natl. Acad. Sci., 85, 2533–2537, 1988). Binding assays, typically with radiolabelled (e.g., $^{3}H$ and $^{125}I$) steroids or ligands, do detect and can be used to determine the binding parameters of biologically active receptors. Other methods of labelling the ligand, such as, for example, with fluorescent groups or with biotin that can be detected by fluorescent spectroscopy or avidin-linked enzyme assays respectively, can also be employed for use in these binding assays. Unfortunately, since the expression of steroid-regulated responses requires many steps that are distal to the binding of steroid to receptor, a lesion in any of these steps can also lead to steroid resistance. Thus, an assay which measures the desired biological response is the most accurate method for determining whether a given cell will respond to steroids. However, measurements of the final response (such as cell death) are often technically very difficult or time consuming. In the treatment of breast cancer, one compromise in this direction has been to determine the presence of "functional" estrogen receptors by measuring the amount of progesterone receptors, which are induced by estrogens (Clark et al., N. Engl. J. Med., 309, 1343–1347, 1983). However, in most other cases, people have settled for the simple assay of steroid binding activity in order to predict the quantity of "functional" receptors.

Initially it was thought that each steroid hormone might bind exclusively to its cognate receptor. This hypothesis has since been found to be incorrect. In fact, it appears to be impossible to find any steroid that will bind to just one type of receptor. Cross-reactivity is especially high with glucocorticoid, progesterone, and mineralocorticoid receptors, which is probably related to the high degree of homology that is seen in the steroid-binding domains of these three receptors (Evans, 1988, supra). Thus various expensive synthetic steroids are required to selectively bind to, or block, one receptor in those many tissues that are known to contain two of these receptors. However, when all three receptors are present in the same tissue, as is the case for pituitary and mammary tissue, it can be very difficult to quantitate the binding to just one receptor.

A different approach to eliminating the problem of cross-reactivity in steroid binding would be to find an inexpensive reagent that would selectively recognize a structural element of the steroid-binding domain that is different for each receptor. The present invention was discovered with the above disadvantages and concerns in mind.

SUMMARY OF THE INVENTION

The present inventor has found that low concentrations of methyl methanethiolsulfonate (MMTS), and very low concentrations of arsenite, specifically and reversibly inactivate all of the steroid-binding activity of glucocorticoid receptors.

By selectively and reversibly blocking the glucocorticoid receptor, the present invention has many uses. The interaction that occurs between glucocorticoid receptors and arsenite or MMTS can be used in assay protocols which have several advantages over the currently available assays.

The present invention is directed to a method for selectively blocking glucocorticoid receptors, which comprises contacting an effective glucocorticoid receptor blocking amount of arsenite or MMTS with a sample containing said glucocorticoid receptors.

In one embodiment, the present invention constitutes an inexpensive reagent for determining the non-specific binding of [$^{3}H$]steroids to solutions of glucocorticoid receptors.

The present invention is also directed to a method of selectively eliminating in a sample the binding of [$^{3}H$]-steroids to glucocorticoid receptors in the presence of other steroid receptors, e.g. progestin and mineralocorticoid receptors, thus allowing the quantitation of these other non-glucocorticoid steroid receptors present in said sample.

More particularly, the present invention is also directed to a method for assaying for progesterone receptors in breast cancer tissue, which comprises contacting a breast cancer tissue sample with an effective amount of arsenite or MMTS to effectively block glucocorticoid receptors present in the tissue sample and then assaying for the presence of progesterone receptors by any conventional means in the breast cancer tissue sample.

This method has particular use in allowing the quantitation of progesterone receptors in breast cancer patients, wherein glucocorticoid, mineralocorticoid and progesterone receptors are all present. Accurately determining the exact number of progesterone receptors in these tissues is very important because the presence and amount of these receptors is of prognosticative value in selecting the best treatment for breast cancer patients.

The present invention is also directed to a method for assaying for mineralocorticoid receptors in a tissue sample which has mineralocorticoid receptors which comprises contacting said tissue sample with an effective amount of arsenite or MMTS to effectively block glucocorticoid receptors present in the tissue sample and then assaying for the presence of said mineralocorticoid receptors by any conventional means in the tissue sample.

Further the present invention is also directed to a method for reversibly blocking glucocorticoid receptors which comprises contacting an effective glucocorticoid receptor blocking amount of arsenite or MMTS to a sample containing said glucocorticoid receptors and then reversing said blocking by contacting said arsenite or MMTS bound glucocorticoid receptors with an effective glucocorticoid liberating amount of a thiol compound, such as dithiothreitol (DTT). This method is useful for studying tissue samples which are available in limited quantities and which need to be recycled for further studies.

Still another embodiment of the present invention is directed to a method for purifying glucocorticoid receptors which comprises immobilizing arsenite on an inert matrix to form an arsenite derivatized inert matrix, contacting a solution containing glucocorticoid receptors with said derivatized matrix thus retaining said glucocorticoid receptors bound to said derivatized matrix, and collecting said glucocorticoid receptors by washing said derivatized matrix with a glucocorticoid receptor liberating amount of a thiol compound.

The present invention is also directed to a test kit for the detection of a first nonglucocorticoid steroid receptor which comprises (a) a container, a bottle or vial of arsenite or MMTS; (b) a container, a bottle or vial of a labeled ligand having specificity for said first nonglucocorticoid receptor; and (c) a container, bottle or vial of a competitive ligand which will block the binding of said labeled ligand in (b) to said first nonglucocorticoid receptor to be detected. Still, a further aspect of the present invention is directed to a test kit for the detection of a first nonglucocorticoid receptor which comprises (a) a container, bottle or vial of arsenite or MMTS; and (b) a container, bottle or vial of at least one blocking reagent which has specificity for a nonglucocorticoid steroid receptor other than said first nonglucocorticoid steroid receptor being detected.

Thus, arsenite and MMTS are new, rapid, reversible, and inexpensive reagents for specifically inactivating the glucocorticoid receptors in the presence of other steroid receptors. Arsenite and MMTS also provide a method for determining the amount of binding to glucocorticoid receptors in the presence of cross-reacting receptors simply by quantitating the binding in the presence and absence of arsenite or MMTS.

BRIEF DESCRIPTION OF THE DRAWINGS

FIG. 1 shows the inhibition of [$^3$H]Dexamethasone ([$^3$H]Dex) binding to HTC, i.e., rat hepatoma tissue culture cell receptors by preincubation with MMTS.

FIG. 1A shows effect of MMTS preincubation time on the inhibition of [$^3$H]Dex binding.

FIG. 1B shows a detailed dose-response curve for the inhibition of [$^3$H]Dex binding after a 2.5-hr preincubation with MMTS.

DETAILED DESCRIPTION OF THE PREFERRED EMBODIMENTS

Chemicals

Figure 2:
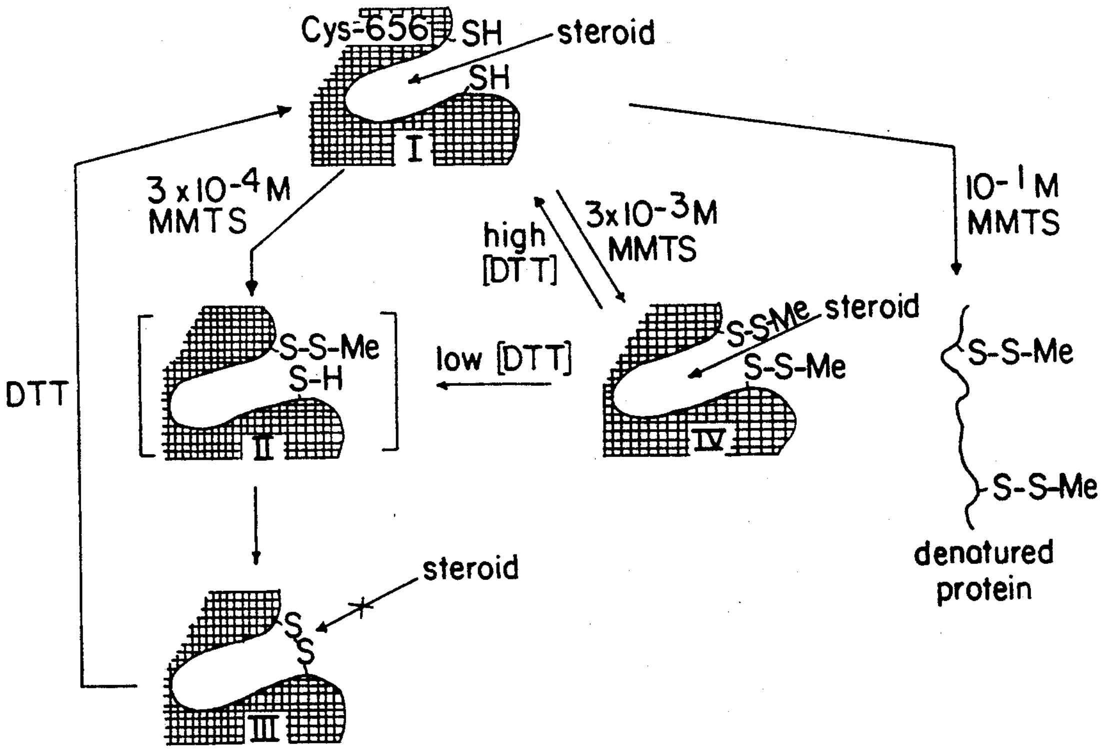
FIG. 2 shows a model of MMTS/DTT modifications of sulfhydryl groups in the steroid binding cavity of glucocorticoid receptors.

[$^1$H]Dex and [$^1$H]estradiol were obtained from Sigma Chemical Co. (St. Louis, Mo). [$^3$H]Dex (40 or 47 Ci/mmol) was obtained from Amersham Corp. (Arlington Heights, Ill). [$^1$H]RU 28362, [$^1$H] and [$^3$H]R5020, i.e., 17,20-dimethyl-19-nor-4,9-pregnadiene-3,20-dione (86 Ci/mmol), [$^3$H]Dex-Mes, i.e., dexamethasone 21-mesylate (37.3 or 49.9 Ci/mmol), and [$^3$H]estradiol (104.4 Ci/mmol) were obtained from DuPont-New England Nuclear (Boston, Mass.). TAPS, i.e., 3[tris(hydroxy methyl)ethyl]aminopropane sulfonic acid (Ultrol grade) was obtained from Cal-Biochem (San Diego, Calif.); sodium arsenite was obtained from Baker (Phillipsburg, N.J.), and sodium selenite pentahydrate was obtained from Fluka (Ronkonkoma, N.Y.). MMTS (stored at 0° C.) and anhydrous cadmium chloride were obtained from Aldrich (Milwaukee, Wis.). Trypsin (tosylphenylalanyl chloromethyl ketone-treated) and soybean trypsin inhibitor were obtained from Worthington (Freehold, N.J.) or Sigma, and lysylendopeptidase C was obtained from Cal-Biochem. 4-Chloro-1-napthol was obtained from Sigma. Reagents for SDS-polyacrylamide gel electrophoresis, including Coomassie Blue R-250 and Tween 20 (EIA grade), were obtained from Bio-Rad (Richmond, Calif.) except for the prestained molecular weight markers, which are obtained from BRL (Gaithersburg, Md.). Fluorescent Ult-Emit autoradiography marker was obtained from DuPont-New England Nuclear. ABC reagent for immunoperoxidase staining of Western blots was acquired from Vector Labs (Burlingame, Calif.).

All [$^3$H]labelled samples were counted in Hydrofluor (National Diagnostics, Manville, N.J.) at 40–55% counting efficiency in a Beckman 5801 liquid scintillation counter with automatic cpm-to-dpm conversion.

Antibodies

Anti-receptor antibody (BUGR-2) was obtained from the Univ. of Arkansas for Medical Science. A polyclonal anti-hsp90 (anti-heat shock protein 90) antibody was obtained from NCI, NIH. The biotinylated anti-mouse and anti-rabbit second antibodies for Western blotting were obtained from Vector Labs.

Buffers and Solutions

TAPS buffer was composed of 25 mM TAPS, 1 mM ethylenediaminetetraacetic acid, and 10% glycerol. The pH of the TAPS buffer was adjusted to 8.2, 8.8, or 9.5 at 0° C. with sodium hydroxide. HEPES, i.e., 4-(2-hydroxyethyl)-1-piperazine ethane sulfonic acid buffer contained 25 mM HEPES, 1 mM ethylenediaminetetraacetic acid, and 10% glycerol and was adjusted to pH 7.5 at 0° C. with sodium hydroxide. Two-fold concentrated SDS sampler buffer contained 0.6M Tris (pH 8.85), 2% SDS, 0.2M DTT, 20% glycerol, and bromphenol blue. Transfer buffer for Western blotting contained 25 mM Tris, 192 mM glycine, 20% methanol in water (pH ~8.3 at room temperature). Tris buffered saline (TBS) was 20 mM Tris and 0.28M NaCl in water (pH=7.5 at room temperature).

All amounts expressed herein are by weight unless expressly stated otherwise. All operations are at 0° C. unless expressly stated otherwise.

The methods of the present invention can be run at temperatures such that the glucocorticoid receptors remain active. Examples of such temperatures are in a range of from about 0° to 10° C. Preferred temperatures are in the ice bath range of from about 0° to 4° C.

The source of arsenite can be obtained from any salt of arsenite which can dissociate in solution to form free arsenite. Examples of such salts include, but are not limited to, sodium arsenite, potassium arsenite and calcium arsenite. Sodium arsenite can be obtained from J. T. Baker Chemical Co., Phillipsburg, N.J. Potassium arsenite can be obtained from La Pine Scientific Co., Chicago, Ill. or Reliable Chemical Co., St. Louis, Mo.

In accordance with the present invention, MMTS or arsenite should be contacted with the sample lysate for a time such as to allow reaction of the MMTS or arsenite with all of the glucocorticoid receptors present in the sample lysate. Of course, this time can vary from sample to sample. Furthermore, MMTS can be contacted with the sample lysate for at least 1 hr and preferably at least 2.5 hrs. Sample lysate is defined as a broken cell extract of the sample cells. When arsenite is used in accordance with the method of the present invention, the arsenite can be contacted with the sample lysate for at least 15 min and preferably 30 min.

Figure 3:
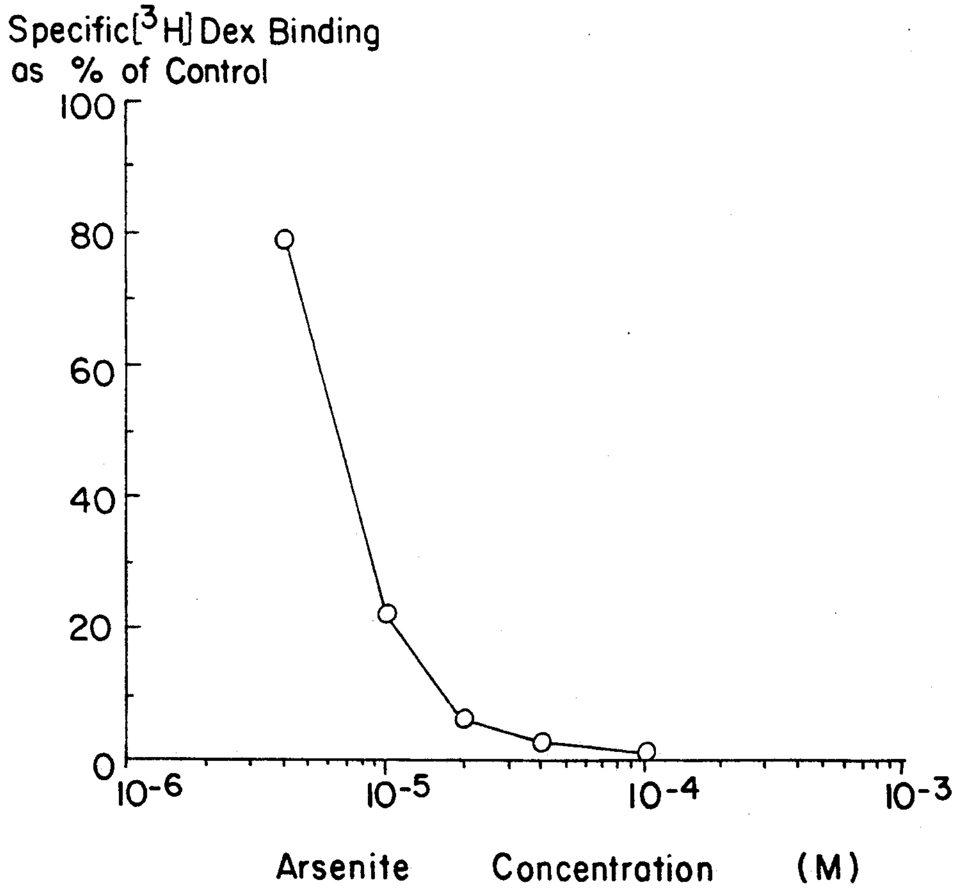
FIG. 3 shows the effect of arsenite preincubation on [$^3$H]Dex binding to steroid-free receptors.
Figure 7:
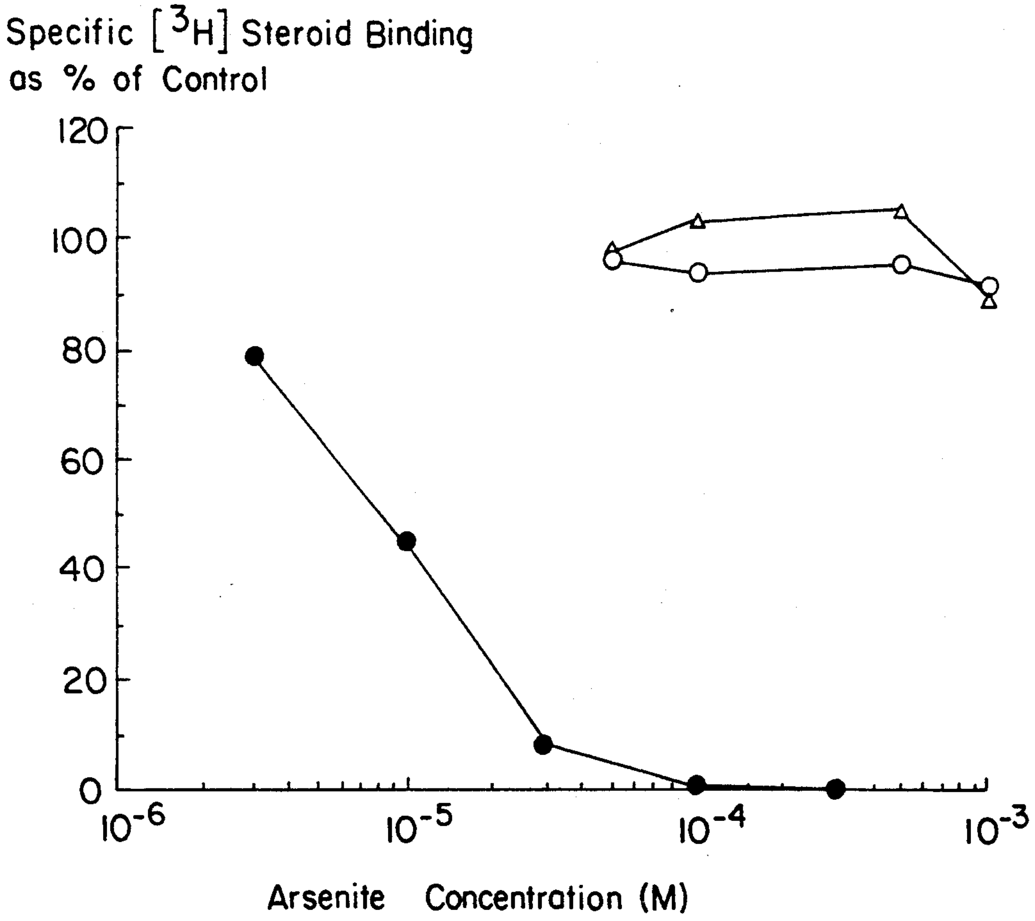
FIG. 7 shows the effect of arsenite on the steroid binding of human glucocorticoid, estrogen, and progesterone receptors.

By glucocorticoid receptor blocking effective amount is meant the concentration of arsenite, or MMTS, for selectively blocking ligand binding to glucocorticoid receptors while not affecting ligand binding to other steroid receptors. This amount depends on several factors which can vary from sample to sample and from preparation to preparation of the same sample. The determination of an optimum amount for each sample varies and is well within the level of skill in the art to ascertain the same without undue burden and experimentation. The most important of these factors appear to be (1) the protein concentration of the sample and (2) the endogenous thiol content of the sample. It is also possible that tissue-specific factors and the slight differences in amino acid sequence of the receptors from different species (e.g., rat vs. human) will make a difference. Variations in any of these factors could be responsible for the minor differences in the dose-inhibition curves for glucocorticoid receptors that are seen in FIGS. 3 and 7. For this reason, a standard inhibition curve for arsenite (such as in FIG. 3), or MMTS (such as in FIG. 1B), should be determined at the beginning of each series of experiments, using preparation conditions that will remain constant throughout the rest of the series. Arsenite concentrations which are useful range between 100 and 500 μM and currently afford the best results (i.e., complete inhibition of glucocorticoid binding with little effect on other receptors). Preferred MMTS concentrations for rat glucocorticoid receptors are approximately 300 μM. However, other systems may require different arsenite, and MMTS, concentrations which can be determined without undue burden and experimentation.

To determine the presence of binding of a particular ligand which is specific to a particular steroid receptor, that ligand may be conjugated to a label which is capable of producing a detectable signal in relation to the presence or absence of the receptor which is specific to the labeled ligand. The label to be conjugated to ligand can be, for example, enzymes, radioisotopes, particles, supports, chromogens, fluorescers, chemiluminescers, coenzymes, free radicals, and bacteriophages. Methods for conjugating labels to ligands are known in the art. See, for example, U.S. Pat. Nos. 3,935,074, 3,996,345, 4,235,869, and 4,720,450 and which are incorporated herein by reference.

Binding assays which are useful for detecting the presence of other steroid receptors include binding assays which typically employ radiolabelled (e.g. $^3H$ and $^{125}I$) steroids or ligands and are well known in the art. Other labelling groups which can be incorporated into the ligand for these assays include, for example, fluorescent groups or biotin which can then be detected by fluorescent spectroscopy or avidin-linked enzyme assays, respectively, both of which are also well known in the art.

The concentration or amount of labeled ligand in vial (b) to be used in the present invention is in excess of the amount of e.g., about equal to five times the $K_d$ of the labeled ligand of vial (b) for the receptor.

The concentration or amount of the competitive ligand in vial (c) to be used in the present invention is in excess of the amount e.g., about equal to 500 times the $K_d$ of this ligand of vial (c) for the receptor.

Examples of thiols useful in liberating the glucocorticoid receptor from arsenite or MMTS according to the methods of the present invention include dithioerythritol (DTE), dithiothreitol (DTT) and β-mercaptoethanol (β-MERC). A preferred thiol is dithiothreitol.

By glucocorticoid liberating effective amount is meant the concentration of a thiol which will reduce the arsenite or MMTS induced complexes with the thiols of the glucocorticoid receptors present, thus effectively dissociating the arsenite or MMTS originally bound to said glucocorticoid receptors. This amount can vary from sample to sample and from preparation to preparation of the same sample. The determination is well within the level of skill in the art.

By arsenite derivatized inert matrix is meant wherein arsenite is bound to an insoluble support matrix via any known linker groups. Arsenite (As) can be in the form Ph-As=0 wherein Ph is a substituted phenyl group. One side of the linker group is attached to the phenyl group, preferably para to the -As=0 group. The other side of the linker group is attached to the insoluble support matrix. An example of such a construct is depicted below

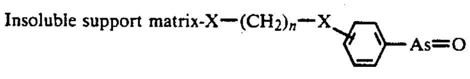

or

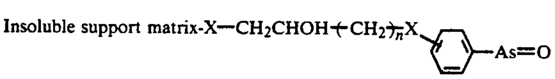

wherein N=0–9 and each of X is the same or different and selected from $CH_2$, O, CONH, NH and S.

Any linking group which is capable of attaching to both the insoluble support matrix and -Ph-As-O would be useful. Such linking groups include but are not limited to groups having the formula $—X—(CH_2)_n—X—$ and $—X—CH_2CHOH—(CH_2)_n—X$ — wherein X=0–9 and wherein each X is the same or different and selected from $CH_2$, O CONH, NH, and S. However, any group which binds to the phenyl group and the support is effective.

Insoluble support matrices which can be used for immobilizing the arsenite of the present invention as discussed above include, but are not limited to, agarose, carboxymethylagarose, cyanogen bromide activated agarose, omega-aminoalkylamino-carboxymethyl agarose, carboxymethylcellulose, aminoethylpolyacylamide, 3-aminopropyldiethoxysilyl silica, chloromethylpolystyrene, epichlorohydrin-activated agarose, thiopropyl cyanogen bromide activated agarose, aminoalkyl cyanogen bromide activated agarose, avidinagarose, or the Sephadex ® type matrices.

The invention also includes kits for carrying out the methods discussed above. In the kit, the reagents can be provided in packaged combination in the same or separate containers. In a first embodiment, the test kit comprises (a) a container, bottle or vial of arsenite or MMTS; and (b) a container, bottle or vial of a labeled ligand which has specificity for a first nonglucocorticoid receptor to be detected; and (c) a container, bottle or vial of a competitive ligand which will block the binding of said ligand in (b) to said first nonglucocorticoid receptor to be detected. The test kit, in accordance with the first embodiment can further include at least one bottle or vial of a blocking reagent which has specificity for at least one nonglucocorticoid receptor other than the first glucocorticoid receptor to be analyzed.

In a second embodiment, the test kit comprises (a) a bottle or vial of arsenite or MMTS; and a bottle or vial of at least one blocking reagent which has specificity for at least one nonglucocorticoid receptor other than the nonglucocorticoid receptor to be analyzed.

By first nonglucocorticoid receptor is meant that nonglucocorticoid receptor for which detection is desired. Examples of nonglucocorticoid receptors which can be detected include estrogen receptors, progestin receptors, mineralocorticoid receptors and androgen receptors.

By competitive ligand is meant any non-labeled ligand which blocks the binding of the labeled ligand to the first nonglucocorticoid receptor to be detected and has specificity for that receptor.

By blocking reagent is meant any ligand which has specificity for the nonglucocorticoid steroid receptors as exemplified above, and which effectively blocks that receptor thus rendering it inactive. By doing so, the labeled ligand which is utilized in detecting the particular nonglucocorticoid receptor (or first nonglucocorticoid receptor) is prevented from binding to the other nonglucocorticoid receptor present in the sample.

Blocking reagents useful in blocking estrogen receptors such as estradiol. Blocking reagents useful for blocking progestin receptors include, but are not limited to ORG 2058 and R5020. Blocking reagents useful for blocking androgen receptors, include but are limited to, 5 α-dihydrotestosterone. Blocking agents useful in blocking mineralocorticoid receptors include, but are not limited to, RU26,752.

The amount of blocking reagent useful is an amount in excess of the amount needed to saturate the particular receptor in question, a determination well within the level of skill in the art. Standard conventional receptor binding assays which utilize labeled ligand and are well-known in the art can be used to detect the desired nonglucocorticoid receptors. The blocking agents for blocking other nonglucocorticoid receptors and the competitive ligand according to the assay, can be added prior to, or at the same time as, the labeled ligand.

The reagent included in the test kits of the present invention may also include other ancillary agents such as buffering agents, if necessary.

Referring to FIG. 1A, duplicate samples of HTC cell (Thompson, E.B., Methods Enzymol., 58, 544–551 [1979]) cytosol solution were pretreated with various concentrations of MMTS in absolute EtOH (final concentration of ETOH=1%) for 0 hr (○), 0.5 hr (●), or 2.5 hr. (◒) before the addition of $[^3H]Dex \pm [^1H]Dex$. After a further 2.5 hr incubation, the free steroid was removed by the addition of dextran-coated charcoal. The specific binding to receptors was determined as described by Miller and Simons, J. Biol. Chem., 263, 15217–15225, 1988) (see also section entitled "Cells and preparation and labelling of receptors" below) and plotted as percentage of the EtOH-pretreated control versus the concentration of MMTS. The data points shown are the average values derived from 1–5 experiments.

Referring to FIG. 1B, duplicate samples of HTC cell cytosol solution were treated with various concentrations of MMTS for 2.5 hr before determining the remaining steroid binding activity of the receptors as described above for FIG. 1A.

Referring to FIG. 2, the hypothetical steroid-binding cavity of the receptor containing part of the receptor protein and Cys-656 is shown. Steroid can bind to the fully reduced, unmodified receptor (I) and to the mixed disulfide form (IV), but not to the intramolecular disulfide form (III) as described by Miller and Simons (1988), supra.

Referring to FIG. 3, steroid-free receptors containing 21 mM $Na_2MoO_4$ were incubated with various concentrations of 100× (in pH 8.8 TAPS buffer) arsenite for 30 min. The binding activity of these receptors was then assayed by incubating with $[^3H]Dex \pm$excess $[^1H]Dex$ for 2.5 hr. The amount of specific binding of $[^3H]Dex$ (determined as described above for FIG. 1A) after arsenite preincubation was expressed as a percent of the untreated control.

Figure 4:
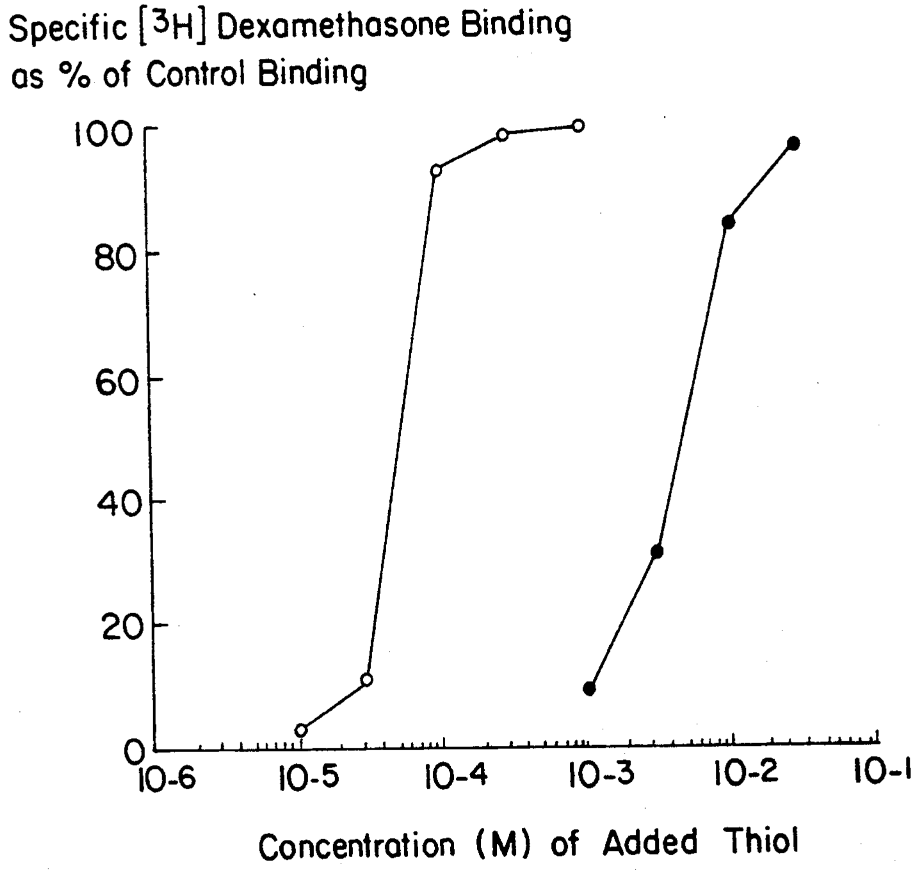
FIG. 4 shows the reversal of arsenite inhibition of steroid binding to steroid-free receptors by DTT and $\beta$-mercaptoethanol ($\beta$-MERC).

Referring to FIG. 4, steroid-free receptors in pH 8.8 TAPS buffer containing 21 mM $Na_2MoO_4$ were preincubated with 40 uM arsenite for 30 min and then adjusted to various concentrations of DTT or β-MERC by addition of 100× solutions of each thiol in pH 8.8 TAPS buffer. After a further 30 min preincubation, the binding activity of these receptors was assayed by incubating with [$^3$H]Dex±excess [$^1$H]Dex for 2.5 hr. The amount of specific binding (determined as described above for FIG. 1A) of [$^3$H]Dex after DTT(o) and β-MERC (●) preincubation was expressed as a percent of the untreated control.

Figure 5:
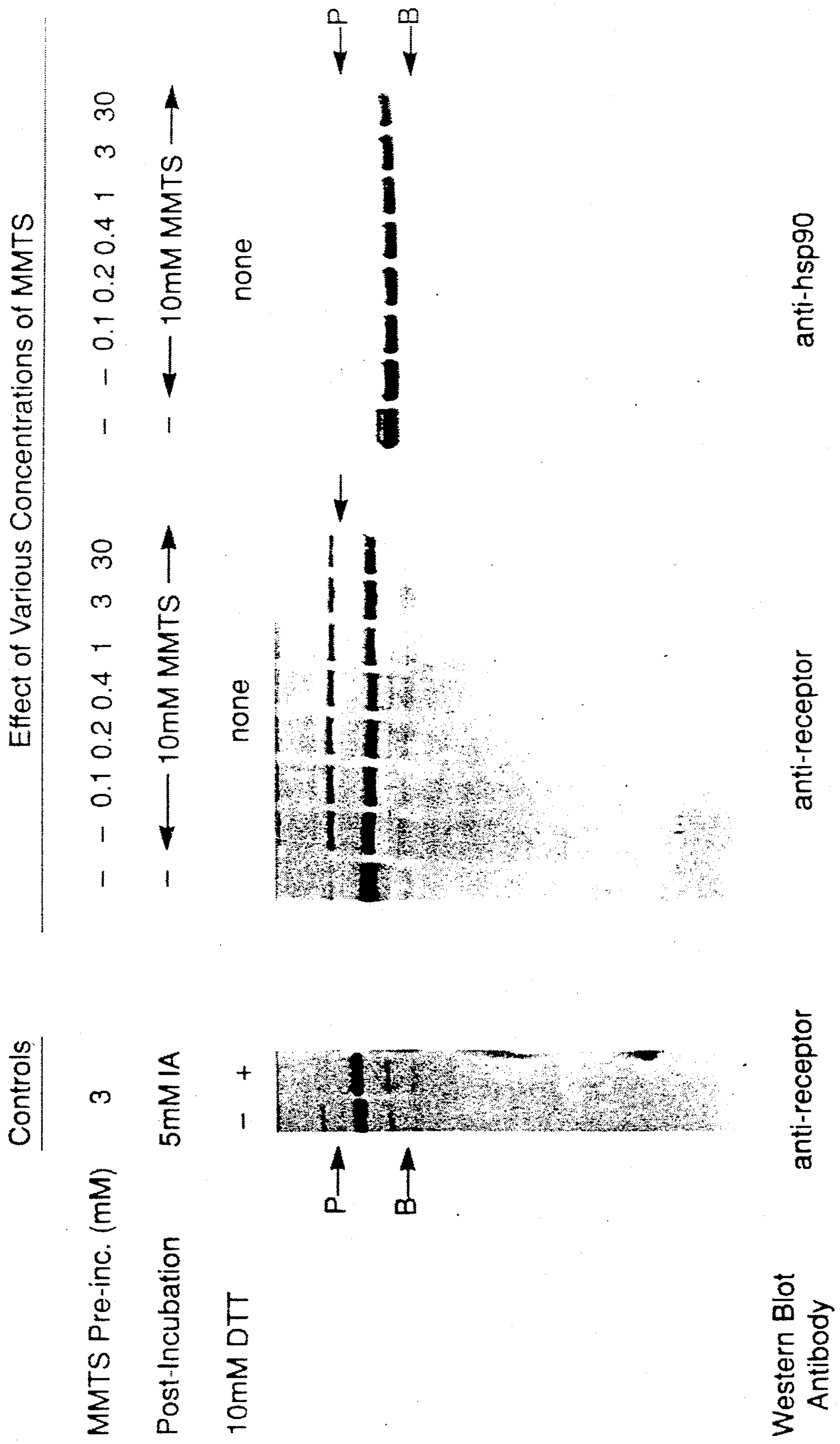
FIG. 5 shows a Western blot analysis on non-reducing SDS-polyacrylamide gels of MMTS-pretreated 98 kDa receptor and hsp90.

Referring to FIG. 5, steroid-free receptors in pH 8.8 TAPS buffer (containing 21 mM $Na_2MoO_4$) were preincubated with various concentrations of arsenite for 30 min and then reacted with either an excess (5 or 10 mM) of iodoacetamide (IA) or MMTS for 30 min to consume all of the remaining free -SH groups. Samples were mixed at room temperature (r.t.) with an equal volume of 2× SDS sample buffer without DTT and subjected to SDS-PAGE (at 15° C.) followed by electrophoretic transfer to nitrocellulose (at r.t.). Western blotting (at r.t.) with a mouse anti-receptor antibody (BUGR-2) or a rabbit anti-hsp90 antibody was visualized by immunoperoxidase staining with biotinylated anti-mouse, or anti-rabbit, second antibodies and ABC reagent (avidin-biotin labelled horseradish peroxidase conjugate) as described by the supplier (Vector Labs). The arrows indicate the positions of the pre-stained molecular weight markers (P=phosphorylase b, B=bovine serum albumin).

Figure 6:
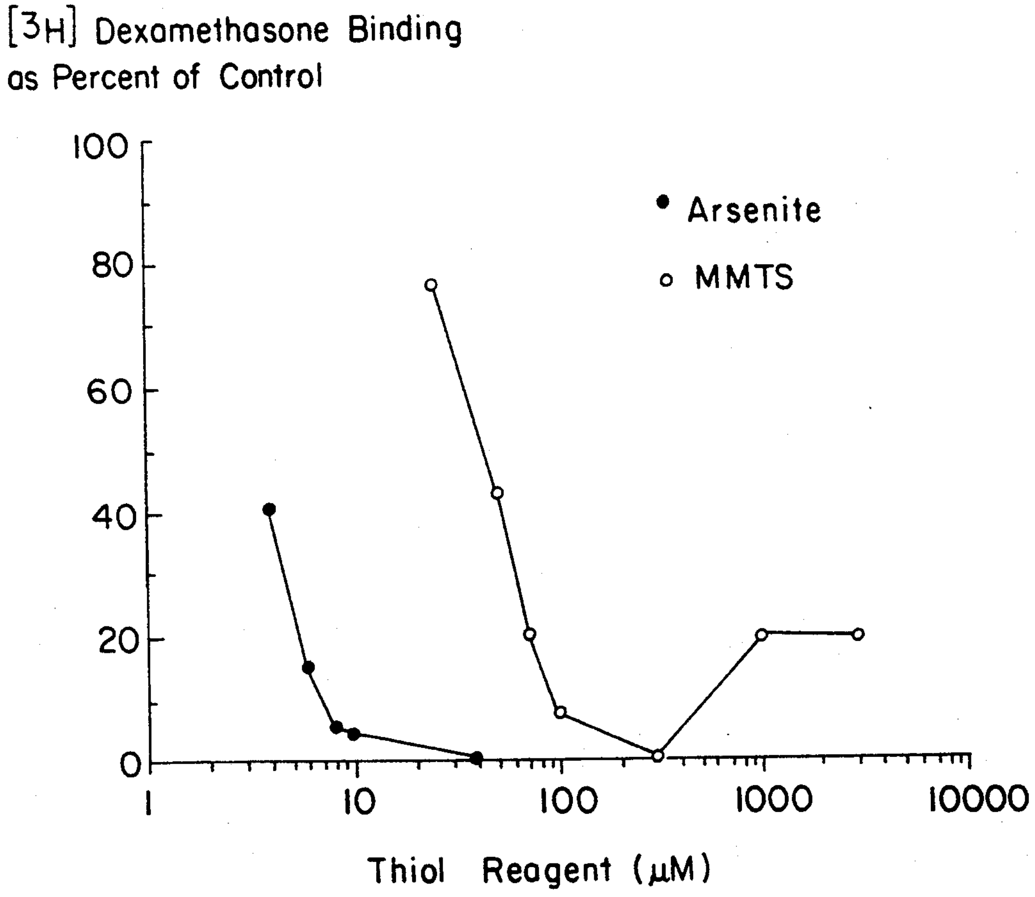
FIG. 6 shows the inhibition of [$^3$H]Dex binding to 16 kDa steroid-binding core fragment of HTC cell receptors by preincubation with arsenite or with MMTS.

Referring to FIG. 6, duplicate samples of steroid-free receptors in pH 8.8 TAPS buffer containing 21 mM $Na_2MoO_4$ were digested with trypsin (14 μg/ml for 1 hr), to generate the 16 kDa core fragment of the receptor, followed by a 10-fold (wt/wt) excess of soybean trypsin inhibitor to block further digestion. The samples were then treated with various concentrations of arsenite (for 30 min) or MMTS (for 2.5 hr) before determining the remaining [$^3$H]Dex binding as described above for FIG. 1A.

Referring to FIG. 7, steroid-free receptors (glucocorticoid, estrogen, and progesterone receptors in MCF-7 cell [from NCI, NIH] cytosol in pH 7.5 HEPES buffer containing 21 mM $Na_2MoO_4$) were treated with various concentrations of 100× (in pH 7.5 HEPES buffer) sodium arsenite for 30 min. The binding activity of these receptors was then assayed by incubating with [$^3$H]steroid±[$^1$H]steroid for 2.5 hr. The amount of specific binding of [$^3$H]steroid (as described above for FIG. 1A) after arsenite preincubation was expressed as the percent of the untreated control for glucocorticoid (●) estrogen (Δ), and progesterone (○) receptors.

The following are examples and are not intended nor should they be interpreted as limiting the scope of the invention.

Cells and Preparation and Labelling of Receptors

The growth of HTC cells at 37° C. in spinner and monolayer cultures of Swim's S77 medium (GIBCO; Grand Island, N.Y.) supplemented with 5% fetal and 5% newborn bovine serum (both obtained from Biofluids; Rockville, Md.) and 0.03% glutamine are described in Thompson, 1979. HTC cell cytosol containing the steroid-free receptors was prepared, stored in liquid $N_2$, and labelled as set forth in Reichman et al., Biochem., 23, 5376–5384, 1984; Simons et al., Biochem., 23, 6876–6882, 1984. Briefly, unless indicated otherwise, 30% cytosol solutions were prepared by mixing three parts cytosol, 2 parts pH 9.5 TAPS buffer, and 5 parts pH 8.8 TAPS buffer (final solution contains $Na_2MoO_4$ at 0 or ~21 mM). Steroid binding (or affinity labelling) was achieved by the addition of 20× stocks of [$^3$H]Dex±550× [H]Dex (final [$^3$H]Dex concentration=3–5×10$^{-8}$M) or of [$^3$H]Dex-Mes±100× [$^1$H]Dex (final [$^3$H]Dex-Mes concentration ~1.5×10$^{-7}$M). After incubation for 2.5 hr, the [$^3$H]Dex-Mes-labelled solutions were quick-frozen at −78° C. for subsequent analysis by SDS-polyacrylamide gel electrophoresis. The specifically bound [$^3$H]Dex was determined by first adding a 10% dextran-coated charcoal solution (added volume=20% of reaction solution volume) to remove free steroid and then subtracting the nonspecific binding seen in the presence of excess [$^1$H]Dex.

MCF-7 cells (obtained from NIH) were grown as monolayer cultures in Richter's IMEM (NIH Media Unit, NIH) (supplemented with 10% fetal bovine serum [Biofluids] and 0.03% glutamine) in an atmosphere of 5% $CO_2$/95% air at 37° C. Crude receptor solutions were prepared by freeze-thaw lysis (in liquid $N_2$) of cells washed in phosphate buffered saline (Reichman et al., 1984; Simons et al., 1984). The cell lysates were treated with either pH 9.5 TAPS or pH 7.5 HEPES buffer (containing 20 mM $Na_2MoO_4$) and centrifuged at 2500×g for 10 min or 100,000×g for 60 min. The supernatants were then used for binding assays as described above, except that pH 7.5 HEPES buffer was used for all of the dilutions and the following steroids were used to detect the other receptors (7×10$^{-9}$M [$^3$H]R5020+210 fold excess [$^1$H]Dex and 7×10$^{-9}$M [$^3$H]R5020+210 fold excess [$^1$H]R5020 for uncompeted and competed binding respectively to progesterone receptors; 7×10$^{-9}$M [$^3$H]estradiol±210 fold excess [$^1$H]estradiol for estrogen receptors).

Partial Purification of Activated [$^3$H]Dex-Mes Labelled Receptors

Activated [$^3$H]Dex-Mes-labelled receptors were purified by DNA-cellulose chromatography in pH 8.2 TAPS buffer containing 500 mM NaCl and stored at −78° C. until used as described by Simons et al. J. Biol. Chem., 258, 2229–2238, 1983; Reichman et al., supra.

Polyacrylamide Gel Electrophoresis

The preparation of samples for reducing gels and the procedures for electrophoresis are described by Simons, J. Biol. Chem., 262, 9669–9675, 1987. For non-reducing gels, the samples were treated with 2× SDS sample buffer lacking DTT. Constant percentage acrylamide gels (10.5–11% with a 1:40 ratio of bisacrylamide to acrylamide) were run in water-cooled (15° C.) Protean II slab gel apparatus (Bio-Rad) at 30 mA/gel (20 mA/gel while in the stacking gel). Gels were fixed and stained in 50% methanol, 7.5% acetic acid containing 0.01% Coomassie Blue R-250, destained in 10% methanol, 7.5% acetic acid, incubated for 1 hr in Enhance (DuPont-New England Nuclear) and 30–60 min in 10% Carbowax PEG 8000 (formerly PEG 6000; Fisher; Springfield, N.J.) with constant shaking at r.t., dried on a Bio-Rad Model 443 slab gel drier at 60° C. with a sheet of dialysis membrane backing (Bio-Rad) directly over the gel to prevent cracking, marked with Ult-Emit at the positions of the molecular weight markers, and fluorographed for 7–12 days at −80° C. with Kodak X-OMAT XAR-5 film.

Western Blotting

After electrophoresis of the samples on SDS-polyacrylamide gels, each gel was equilibrated in transfer buffer for at least 30 min at r.t. Electrophoretic transfer to nitrocellulose was conducted in a well ventilated area at r.t. (or at 4° C.) in a Transblot (BioRad) apparatus for approximately 15 hr at 100 mA and then at approximately 250 mA for 90 min. The nitrocellulose was stained with Ponceau S solution (0.5% Ponceau S [Sigma] and 1% glacial acetic acid in water) to visualize the transferred protein, incubated with blocking solution (2% Carnation non-fat dried milk in TBS, i.e., Tris buffered saline) for 45 min, and washed with 0.1% Tween in TBS (TTBS) for 15 min. Primary antibody (diluted 1:1000[BUGR-2] or 1:50 [anti-hsp90 antibody] in TTBS) was added for ≧2 hr and then removed with 3×5 min washes of TTBS. The incubation with secondary antibody and the subsequent immunoperoxidase staining with ABC reagent were conducted as recommended by Vector Labs.

EXAMPLE 1

Selection of the best treatment program for breast cancer patients usually requires an accurate determination of the number of progesterone receptors (PR) in the breast cancer tissue that will specifically bind radioactively labelled progestins. However, such tissues are reported to contain other receptors in addition to PR; and, virtually all steroids will bind to more than one class of receptor. Thus an accurate quantitation of PR requires blocking the binding of radioactively labelled progestins to the other receptors without influencing the binding to the PR itself. Depending on the concentration of the other receptors, this can be very difficult since there are no known progestins that bind just to the progesterone receptor. A particularly troublesome combination is the presence of the receptors for progestins (PR), mineralocorticoids (MR), and glucocorticoids (GR).

The following procedure is performed at 0° C. Cytosolic solutions (or tissue sample lysates) containing the steroid receptors are prepared by cell rupture (e.g., freezing the sample in liquid nitrogen) followed by the addition of a pH 7.5 buffer (e.g., the pH 7.5 HEPES buffer described above, without added thiols, such as DTT, because they block the action of arsenite and of MMTS, and with sodium molybdate, to stabilize the receptors) and then subjected to centrifugation (from 5,000 to 200,000×g) to remove the nuclei, cell membranes, and other cellular organelles. The cytosol is then treated for 30 min with a 100× stock of sodium arsenite in the same buffer to give a final concentration of ~100 uM. Aliquots of the pretreated solution of receptors are then incubated for at least 2 hr with radioactively labelled progestin (e.g., R5020 or ORG 2058) plus an excess of a non-radioactive steroid, such as aldosterone, fluorocortisone and RU 26,752 to block progestin binding to the mineralocorticoid receptor, with or without an excess of the non-radioactive progestin to determine the non-specific binding of the radioactive progestin. Dextran-coated charcoal (DCC) is then added to remove the free radioactive progestin. After centrifugation at approximately 3000×g for 10 min to pellet the DCC, the dpms of macromolecularly bound radioactive progestin in the supernatant are quantitated by liquid scintillation counting at r.t. The difference in dpms in the tubes±excess non-radioactive progestin represents the specific binding to progesterone receptors without any contribution of binding to glucocorticoid or mineralocorticoid receptors.

EXAMPLE 2

The experimental procedure is basically the same as for Example 1 but a radioactive mineralocorticoid, such as aldosterone, is used to bind to the mineralocorticoid receptors, non-radioactive aldosterone is used to determine the non-specific binding of radioactive aldosterone, arsenite is used to eliminate any binding by glucocorticoid receptors, and a non-radioactive progestin such as R5020 is used to block the binding of progesterone receptors.

EXAMPLE 3

The current efforts in basic research to describe the molecular reactions and interactions of glucocorticoid receptor-steroid complexes involved in activation, binding to specific DNA sequences, and regulation of gene transcription would greatly benefit from a ready source of pure, or even partially purified, receptor-steroid complexes.

An immobilized derivative of arsenite would be used to selectively react with, and remove from solution, the glucocorticoid receptor. Examples of such immobilized derivatives are Ph-As=0, wherein Ph=substituted phenyl group with the substituent preferably para to the -As=0, attached to the phenyl group. Examples of such substituents are spacer arms such as —O—, —$CH_2$—, —CHHCHOH—$CH_2$—X wherein X is —OH, —$NH_2$, and —SH which are used to attach the Ph-As=0 to an insoluble matrix, such as agarose or Sephadex. Examples of preferred immobilized derivatives of the formula

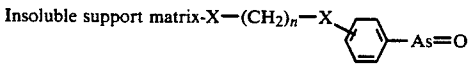

or

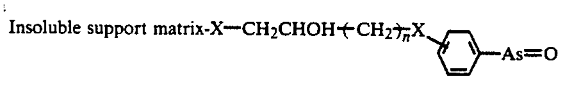

wherein x=0–9, and wherein X is the same or different and selected from $CH_2$, O, CONH, NH, or S are suggested. This procedure would not give total purification but it would give substantial purification. The proposed methodology is as follows.

A solution of crude glucocorticoid receptor (with 20 mM $Na_2MoO_4$ but without added thiols, which prevent the reaction of Ph-As=0 with the vicinal dithiols of the receptor) is incubated with the insoluble matrix containing attached Ph-As=0 for ≧30 min at 0° C. The matrix is then poured into a column and washed extensively with pH 7.5 HEPES buffer described above with sodium molybdate, but without thiols, to remove the loosely associated proteins. The retained glucocorticoid receptors are then released by elution of the column with buffer and a suitable amount of thiol such as DTT (the exact concentration of DTT will depend largely on the concentration of Ph-As=0 on the matrix), and optionally containing sodium molybdate. These receptors are then ready for immediate binding of the desired ligand and subsequent use in almost all experiments that are currently conducted with receptors.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

I claim:

1. A method for selectively blocking glucocorticoid receptors, which comprises contacting an amount of arsenite effective for selectively blocking ligand binding to glucocorticoid receptors while not affecting ligand binding to other steroid receptors with a sample containing said glucocorticoid receptors for a time sufficient to selectively block said glucocorticoid receptors.

2. A specific binding method for selectively blocking glucocorticoid receptors and assaying for other steroid receptors which comprises:

(a) contacting an amount of arsenite effective for selectively blocking ligand binding to glucocorticoid receptors while not affecting ligand binding to other steroid receptors, with a sample containing said glucocorticoid receptors and other steroid receptors for a time sufficient to selectively block said glucocorticoid receptors; and (b) assaying for the presence of said other steroid receptors present in said sample.

3. The method according to claim 2, wherein the binding of [$^3$H]steroids is assayed.

4. The method according to claim 1, which further comprises reversing said binding by contacting said arsenite blocked glucocorticoid receptors conditions and for a time sufficient with an effective amount of a thiol compound for liberating said arsenite from said arsenite bound glucocorticoid receptors.

5. A specific binding method for assaying for progestin receptors in breast cancer tissue which comprises contacting a breast cancer tissue sample with an effective amount of arsenite to effectively block glucocorticoid receptors present in said tissue sample; and detecting the presence of progestin receptors in said breast cancer tissue sample.

6. A specific binding method for assaying for mineralocorticoid receptors in a tissue sample having a glucocorticoid receptors which comprises contacting said tissue sample with an effective amount of arsenite to effectively block glucocorticoid receptors present in said tissue sample; and detecting the presence of said mineralocorticoid receptors in said tissue sample.

7. The method according to claim 5 wherein said breast cancer tissue sample is a breast cancer tissue lysate.

8. The method according to claim 6 wherein said tissue sample is a tissue lysate.

9. A test kit for the detection of a first nonglucocorticoid steroid receptor which comprises:

(a) a container or arsenite; and (b) a container of a labeled ligand having specificity for said first nonglucocorticoid receptor.

10. The test kit according to claim 9 further containing (c) a container of a competitive ligand which will block the binding of said labeled ligand in (b) to said first nonglucocorticoid receptor to be detected.

11. The test kit according to claim 9 wherein said first nonglucocorticoid receptor is an estrogen receptor.

12. The test kit according to claim 9 wherein said first nonglucocorticoid receptor is an progestin receptor.

13. The test kit according to claim 9 wherein said first nonglucocorticoid receptor is an mineralocorticoid receptor.

14. The test kit according to claim 9 wherein said first nonglucocorticoid receptor is an androgen receptor.

15. The test kit according to claim 9 wherein said label is selected from the group consisting of enzymes, radioisotopes, particles, supports, chromogens, fluorescers, chemiluminescers, coenzymes, free radicals, and bacteriophages.

16. The test kit according to claim 9 further comprising at least one blocking reagent which has specificity for a nonglucocorticoid steroid receptor other than said first nonglucocorticoid steroid receptor being detected.

17. The test kit according to claim 16 wherein said blocking reagent effectively blocks progestin receptors.

18. The test kit according to claim 16 wherein said blocking reagent effectively blocks mineralocorticoid receptors.

19. The test kit according to claim 16 wherein said blocking reagent effectively blocks androgen receptors.

20. The test kit according to claim 16 wherein said blocking reagent effectively blocks estrogen receptors.

21. A test kit for the detection of a first nonglucocorticoid receptor which comprises:

(a) a container arsenite; and (b) a container of at least one blocking reagent which has specificity for a nonglucocorticoidsteroid receptor other than said first nonglucocorticoid steroid receptor being detected.

22. A test kit according to claim 21 wherein said blocking reagent effectively blocks progestin receptors.

23. The test kit according to claim 21 wherein said blocking reagent effectively blocks mineralocorticoid receptors.

24. The test kit according to claim 21 wherein said reagent effectively blocks androgen receptors.

25. The test according to claim 21 wherein said blocking reagent effectively blocks estrogen receptors.

* * * * *